(12) United States Patent
Anand et al.

(10) Patent No.: US 9,398,851 B2
(45) Date of Patent: Jul. 26, 2016

(54) RETINAL IMAGING DEVICE

(75) Inventors: Sivaraman Anand, Bangalore (IN);
Kummaya Pramod, Bangalore (IN);
Nagarajan Shanmuganathan,
Bangalore (IN)

(73) Assignee: Remidio Innovative Solutions Pvt. Ltd., Karnataka (IN)

( * ) Notice: Subject to any disclaimer, the term of this patent is extended or adjusted under 35 U.S.C. 154(b) by 0 days.

(21) Appl. No.: 14/002,339

(22) PCT Filed: Aug. 28, 2011

(86) PCT No.: PCT/IB2011/053764
§ 371 (c)(1),
(2), (4) Date: Feb. 11, 2014

(87) PCT Pub. No.: WO2012/176026
PCT Pub. Date: Dec. 27, 2012

(65) Prior Publication Data
US 2014/0146288 A1    May 29, 2014

(30) Foreign Application Priority Data
Jun. 24, 2011  (IN) .......................... 2143/CHE/2011

(51) Int. Cl.
*A61B 3/14* (2006.01)
*A61B 3/15* (2006.01)
(Continued)

(52) U.S. Cl.
CPC ............... *A61B 3/158* (2013.01); *A61B 3/0008* (2013.01); *A61B 3/156* (2013.01); *A61B 3/12* (2013.01)

(58) Field of Classification Search
CPC .. A61B 3/0008; A61B 3/0083; A61B 3/1015; A61B 3/112; A61B 3/12; A61B 3/1208; A61B 3/15; A61B 3/156; A61B 3/158

USPC .......... 351/204, 205, 206, 207, 218, 220, 221
See application file for complete search history.

(56) References Cited

U.S. PATENT DOCUMENTS 887,032 A    5/1908  Zeng
4,249,802 A  2/1981  Muchel et al.
(Continued)

FOREIGN PATENT DOCUMENTS

| CN | 101190121 | 6/2008 |
|---|---|---|
| CN | 101254092 | 9/2008 |
| WO | WO 2012/176026 | 12/2012 |

OTHER PUBLICATIONS

PCT International Patent Application No. PCT/IB2011/053764 filed on Aug. 28, 2011 in the name of Anand et al., International Search Report mailed Jan. 9, 2012.

*Primary Examiner* — Huy K Mai
(74) *Attorney, Agent, or Firm* — Levine Bagade Han LLP

(57) ABSTRACT

A retinal imaging device and illumination module. The illumination module includes a light source to provide an incident beam along an illumination axis, a condenser lens at a spaced apart distance from the light source for condensing the incident beam and emanating a condensed incident beam, a transparent plate at a spaced apart distance from the condenser lens, wherein the transparent plate comprises a light absorber, at least one projections lens system to focus the condensed incident beam, a shield at a spaced apart distance from the projection lens system to yield a first partially blocked beam to form a cornea illumination doughnut, and a perforated mirror comprising a hollow cylinder. A portion of the hollow cylinder protrudes out from a reflecting face of the mirror, forming an elliptical stopper to yield a second partially blocked beam to form a pupil illumination doughnut, enabling reflex-free imaging of the retina.

26 Claims, 4 Drawing Sheets

(51) Int. Cl.
*A61B 3/00* (2006.01)
*A61B 3/12* (2006.01)

(56) References Cited

U.S. PATENT DOCUMENTS

| | | | | |
|---|---|---|---|---|
| 5,479,221 A | * | 12/1995 | Heine et al. | 351/214 |
| 5,914,771 A | * | 6/1999 | Biber | 351/221 |
| 7,467,870 B2 | * | 12/2008 | van de Kraats et al. | 351/221 |
| 2004/0207811 A1 | | 10/2004 | Elsner | |
| 2007/0030449 A1 | | 2/2007 | Liang | |
| 2007/0139613 A1 | | 6/2007 | Tanifuji et al. | |
| 2008/0002152 A1 | | 1/2008 | Collins et al. | |
| 2008/0123050 A1 | | 5/2008 | Tanaka et al. | |
| 2008/0212027 A1 | | 9/2008 | Shimizu | |
| 2009/0244483 A1 | | 10/2009 | Yoshino et al. | |
| 2010/0128221 A1 | | 5/2010 | Muller et al. | |
| 2010/0309431 A1 | | 12/2010 | Itoh et al. | |

* cited by examiner

RETINAL IMAGING DEVICE

CROSS-REFERENCE TO RELATED APPLICATIONS

This application is a U.S. National Phase under 35 U.S.C. 371 to PCT International Patent Application No. PCT/IB2011/053764 filed on Aug. 28, 2011 which claims benefit of priority to Indian Patent Application No. 2143/CHE/2011 filed Jun. 24, 2011, the contents of both of which are incorporated herein by reference in its entirety.

TECHNICAL FIELD

The invention relates generally to a retinal imaging device and more specifically to an imaging of the fundus.

BACKGROUND

Ophthalmoscopy (funduscopy or fundoscopy) is a test that allows a clinician to see inside the fundus of the eye and other structures using an ophthalmoscope (or funduscope). It is done as part of an eye examination and is crucial in determining the health of the retina and the vitreous humor. A Direct Ophthalmoscope produces an upright, or unreversed, image of approximately 15 times magnification. The indirect ophthalmoscope produces an inverted, or reversed, direct image of 2 to 5 times magnification and allows for wider view of the inside of the eye that is useful in detecting several eye related diseases like glaucoma, diabetic retinopathy or eye related imperfections like retinal detachment etc. A diagrammatic representation of the eye is shown in FIG. 1 with the key features of the eye 10 as pupil 12, cornea 14, iris 16, anterior chamber 18, posterior chamber 20, eye lens 22, retina 24, and vitreous humour 26, fovea 28 and optic disc 30. The fundus 32 of the eye is the interior surface of the eye, opposite the lens, and includes the retina, optic disc, macula and fovea, and a few other features.

One of the important aspects in the development of retinal imaging devices relates to solving the issue of the reflections from cornea and the illumination lens. To solve this issue, the Gullstrand Principle for reflex-free ophthalmoscope has been employed in several versions of the eye imaging devices. The principle broadly involves separating the entrance and exit of light in the plane of the pupil of the eye. Therefore the paths of illumination and imaging need to be separated from the cornea to the pupil. More specifically the light entering the eye and imaging light coming out of the eye at the anterior segment (between front of cornea till back of lens) needs to have separate paths. Some exemplary developments in this field are listed below.

U.S. Pat. No. 3,594,071 describes an ophthalmoscopic camera which can eliminate undesired light reflected from the cornea of an eye to be examined and the front and back surfaces of a front objective through which the illumination light passes by interposing a ring-shaped aperture between a plane reflecting mirror and a condenser lens arranged next to the reflecting mirror and a small shield between said condenser lens and the next condenser lens so as to shield a small area in the vicinity of and including the optical axis. The optical system for photography includes no such shield as described above and said photographic objective is of biconvex, thereby increasing the picture angle to 45.degree U.S. Pat. No. 5,713,047 provides an eye fundus photographing apparatus that has an illumination system for illuminating an eye fundus under test by an illumination light beam, a photographing system for photographing the eye fundus under test by a photographing light beam from the eye fundus under test illuminated by the illumination system, and a light shielding member arranged at a vicinity of the illumination diaphragm or the photographing diaphragm or at a vicinity of a conjugate position of the diaphragms, such that the eye fundus photographing apparatus enables eye fundus photographing to be in a good condition to an eye under test having a small pupil diameter.

U.S. 5,572,266 describes a fundus camera capable of adjusting a working distance between a camera body and a subject's eye quickly and easily with high accuracy and capable of observing an eye fundus image in a field of view and at a magnification each substantially same as those selected when an eye fundus is photographed. To adjust the working distance quickly and easily with high accuracy, the fundus camera has an optical member provided in a projecting optical system for projecting alignment light onto a subject's eye. The optical member projects split alignment images onto the eye when the working distance is out of a predetermined proper distance. To observe the eye fundus image in the substantially same field of view and at the substantially same magnification as those selected when the eye fundus is photographed, the fundus camera has a device for, according to power variation, changing a state of illumination light illuminating the eye. In the fundus camera, the alignment light is projected onto the eye, the alignment light reflected by the eye is once converged on a point of a photographic optical path conjugate with the fundus of the eye, the reflected alignment light converged thereon is guided to a TV monitor through a variable power lens, and the state of the illumination light illuminating the eye is changed by the changing device to observe and photograph the eye fundus.

U.S. Pat. No. 4,838,680 describes an optical system for a retinal camera that comprises objective lens adapted to be located toward a patient's eye. The retina of the patient's eye is illuminated and photographed through the objective lens, which has a first biconvex type lens means and a second biconvex type lens means with a space between them, the first biconvex type lens means has a curvature radius of the first convex surface open to the air and faces toward the eye of which is larger than that of the other second convex surfaces open to the air, and the second biconvex type lens means of which curvature radius of third convex surface open to the air and facing toward the first biconvex type lens means is larger than that of the other fourth convex surfaces open to the air.

U.S. Pat. No. 6,546,198 describes a fundus camera that includes a main unit equipped with an illuminating optical system for illuminating the fundus of an eye to be inspected and a photographing optical system for photographing the fundus, an observation optical system for determining whether or not the distance between the main unit and the eye is equal to a proper working distance, an alignment index projecting system, and a driving mechanism for moving a light guide along an optical axis to change a working distance in the case of photographing the central part of the fundus and in the case of photographing a peripheral part of the fundus.

U.S. Pat. No. 7,275,826 describes an apparatus for obtaining an image of the eye, whereon the apparatus comprises a light source for providing an incident illumination and an apertured mirror for directing at least a portion of the incident illumination along an optical axis. A curved objective mirror directs the incident illumination received along the optical axis toward the retina of the eye and directs image-bearing light reflected from the retina back along the optical axis. The apertured mirror transmits the image-bearing light reflected from the retina toward a sensor for obtaining an image of the retina thereby.

U.S. Pat. No. 6,296,358 provides an ocular fundus imager that automatically aligns fundus illuminating rays to enter the pupil and to prevent corneal reflections from obscuring the fundus image produced. Focusing the produced fundus image is automatically performed and is based upon the fundus image itself. A head restraint for the patient undergoing examination is in the form of a pair of spectacles which is not only easy to use accurately but significantly reduces the gross alignment between the optical system and the patient's pupil.

U.S. Pat. No. 4,874,236(A) describes another ophthalmologic apparatus for fundus examination comprising a base, an illumination device and a microscope carried by the base and rotatable about a vertical axis, a fixture for the patient's head and eyes with respect to the vertical axis and a lens positioned at the upper end of the vertical rod in the optical axis of the microscope and the examined eye and displaced from the vertical axis towards the examined eye such as to image the retina of the examined eye at a location for reimaging it by the microscope.

U.S. Pat. No. 4,235,529 describes an apparatus for taking photographs of crystalline lens sections including a slit illumination system and a photographing optical system which includes an optical axis inclined with respect to the slit illumination plane. In order to eliminate an image of illumination light source which may be produced by a light reflected at the patient's cornea, a light interrupting blade member is provided in the illumination optical path at a side of the slit axis adjacent to the photographing optical system.

Though fundus imaging devices have evolved and there have been several improvements in devices for imaging the eye, most of them require high level of operator skill and complex instrumentation. One significant issue that continues to be a problem is the need to eliminate artifactual reflections from the patient's eye as well as from the lens surfaces used in the optical design of the illuminating and imaging apparatus itself, using as simple and compact an optical design as possible. Unless the level of these artifactual reflections is reduced significantly, the overall image quality and image contrast is affected. Current prior art, for example the use of crossed polarizers (see U.S. Pat. No. 7,275,826 FIG. 1 for prior art discussion), eliminates the background reflections to some extent but also significantly reduce the reflectance signal from the retina as well. The use of one or more ring shields in front of the illuminating source (see U.S. Pat. No. 3,594,071 FIG. 1), help reduce the reflections, but increase the size of the optical illumination path. The use of simple perforated mirrors have helped separate the imaging and illumination paths, but can in some design embodiments result in both surface reflections as well as stray illumination reflections from still reaching the imaging sensor/imaging eyepiece. Thus there continues to be a need for further improvement that can help reduce unwanted reflections to improve image quality while keeping the overall optical design of the system, simple and compact.

BRIEF DESCRIPTION

In one aspect, the invention provides an illumination module for a retinal imaging device. The illumination module includes a light source to provide an incident beam along an illumination axis, a condenser lens placed at a spaced apart distance from the light source for condensing the incident beam and emanating a condensed incident beam, a transparent plate placed at a spaced apart distance from the condenser lens, wherein the transparent plate comprises a light absorber in the form of a black dot, at least one projection lens to focus the condensed incident beam, a shield placed at a spaced apart distance from the projection lens to yield a first partially blocked beam to form a cornea illumination doughnut, and a perforated mirror comprising a hollow cylinder. The perforated mirror is at an angle with respect to the illumination axis and the hollow cylinder is placed perpendicular to the illumination axis and at least a portion of the hollow cylinder protrudes out from a reflecting face of the mirror, forming an elliptical stopper to yield a second partially blocked beam to form a pupil illumination doughnut. The cornea illumination doughnut and the pupil illumination doughnut are aligned in a plane perpendicular to the illumination axis. The use of the protruding hollow cylinder helps significantly reduce unwanted reflections from intraocular lens and the cornea, separates the imaging and illumination paths, and helps create a suitable illumination doughnut, to ensure a high quality reflex-free image.

In another aspect, the invention provides a retinal imaging device that includes the illumination module as described herein above and an imaging module.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As used herein and in the claims, the singular forms "a," "an," and "the" include the plural reference unless the context clearly indicates otherwise.

Figure 1:
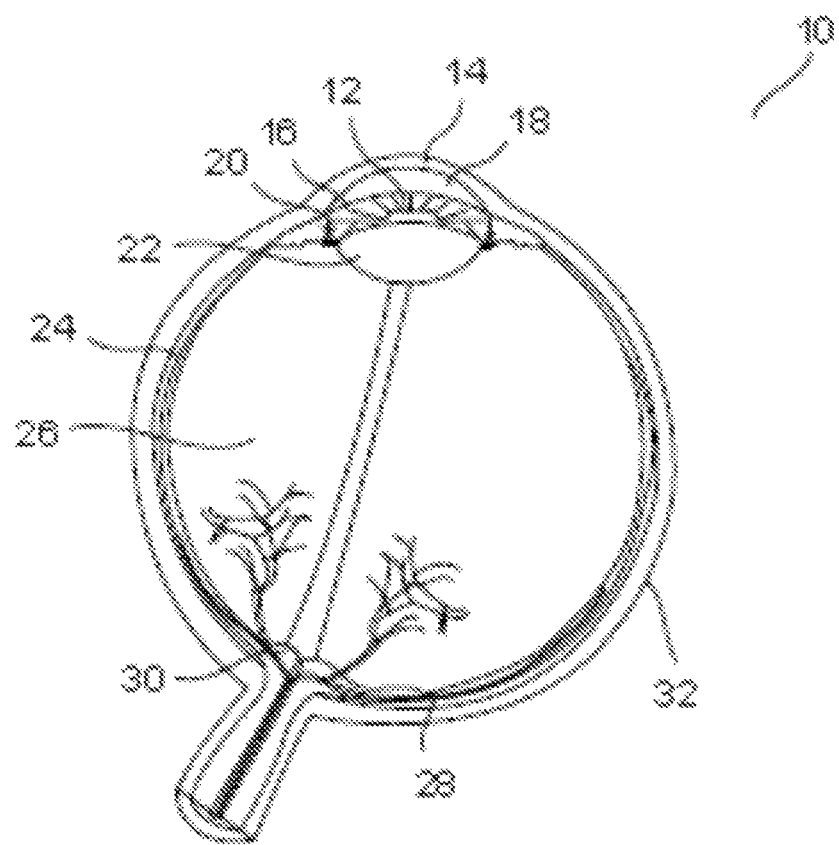
FIG. 1 is a diagrammatic representation of an eye and its internal features useful for understanding the invention.
Figure 2:
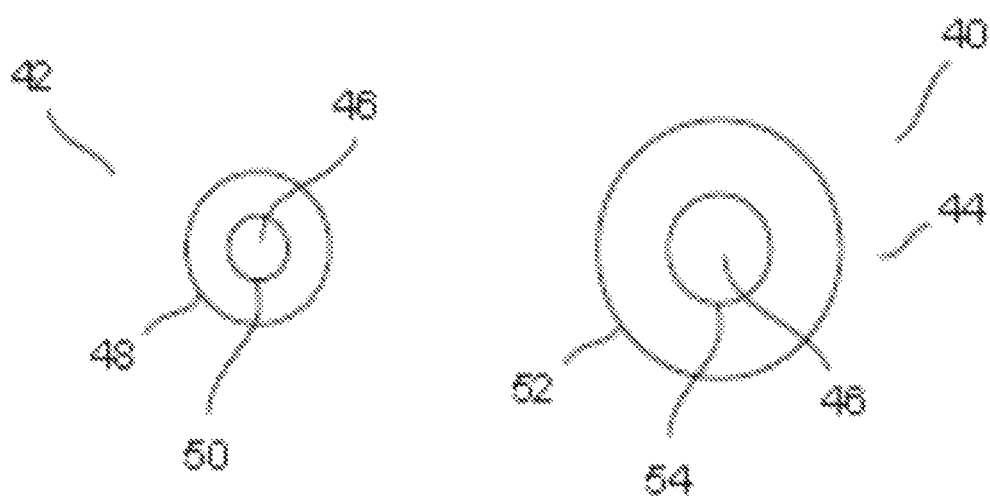
FIG. 2 is a diagrammatic representation of a cornea illumination doughnut and a pupil illumination doughnut as referred in the exemplary embodiments.

The aspects of the invention use the Gullstrand principle as mentioned herein above to illuminate and image the retina in novel configurations and methods. In order to obtain a reflection free image, the retinal imaging device of the invention forms two annular imaging rings, one at cornea plane and the other at pupil plane. FIG. 2 is a diagrammatic representation 40 of the two doughnut rings 42 and 44 that are formed at a cornea plane and a pupil plane respectively. As shown, the doughnut ring 42 at the cornea is smaller then the doughnut ring 44 formed at the pupil facilitating imaging of the eye. The imaging is done through the centre dark spot 46 of the doughnut rings to avoid reflections. Each of the doughnut rings 42 and 44 have an outer boundary and inner boundary, shown generally by 48, and 50 for the cornea doughnut ring and 52, and 54 for the pupil doughnut ring. The formation of these doughnut rings is enabled by the novel illumination module as is described in more detail in reference to FIG. 3.

Figure 3:
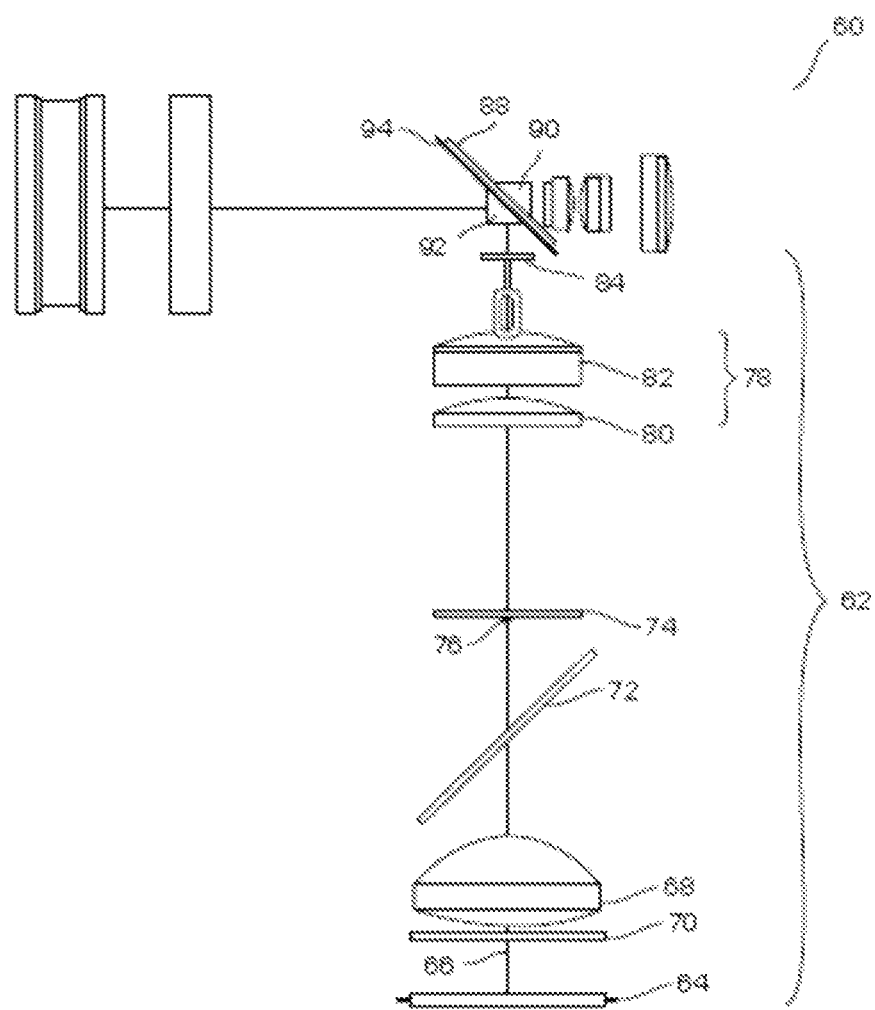
FIG. 3 is a diagrammatic representation of an exemplary embodiment of an illumination module for a retinal imaging device.

FIG. 3 is a diagrammatic representation of the retinal imaging device 60 having an illumination module 62 for a retinal imaging device of the invention. The illumination module 62 includes a light source 64 to provide an incident beam along an illumination axis 66. The light source may be a light emitting diode (LED), a flash tube, a halogen lamp and other like light sources, including laser light sources The light source is characterized by a relatively small size and low heat generation capacity. The illumination module 62 further includes a condenser lens 68 placed at a spaced apart distance from the light source 64 for condensing the incident beam. The condenser lens may be an Abbey lens, aplanatic lens, or achromatic lens. The condenser lens is corrected for spherical and chromatic aberrations in the exemplary embodiment, as would be appreciated by those skilled in the art. In one specific example, a diffuser 70 may be placed between the light source 64 and the condenser lens 68 and a beam splitter 72 may be placed after the condenser lens 68 for improving the characteristic of the incident beam and the condensed incident beam respectively, and to allow for the use of multiple illumination light sources The illumination module 62 further includes a transparent plate 74 placed at a spaced apart distance from the condenser lens 68. In one exemplary embodiment the transparent plate 74 comprises a light absorber 76. In a specific example the transparent plate 74 is a glass plate, the light absorber is a black dot placed in the centre of the glass plate.

The illumination module 62 further includes at least one projection lens system 78 to focus the condensed incident beam. The projection lens system 78 in one example includes a planar lens 80 for example a plano convex lens and a doublet lens 82. The illumination module 62 further includes a shield 84 placed at a spaced apart distance from the projection lens system 78 to yield a first partially blocked beam to form a cornea illumination doughnut 86. The illumination module 62 further includes a perforated mirror 88 comprising a hollow cylinder 90, wherein the perforated mirror 88 is at an angle with respect to the illumination axis 66 and wherein the hollow cylinder 90 is placed perpendicular to the illumination axis 66 and at least a portion of the hollow cylinder depicted generally by 92 protrudes out from a reflecting face of the perforated mirror 88, forming an elliptical stopper 94 to yield a second partially blocked beam to form a pupil illumination doughnut 96. As would be appreciated by those skilled in the art, the cornea illumination doughnut 86 and a pupil illumination doughnut 96 are aligned in a plane perpendicular to the illumination axis 66. The outer diameter of the projection lens system 78 and the diameter of the shield 84, determine the dimensions and characteristics of the cornea illumination doughnut. The projected diameter of the outer elliptical stopper 94 at the porosity mirror and the diameter of the protruding hollow cylinder, determine the diameter of the pupil illumination doughnut. The illumination module as described herein may be battery powered or alternately may be configured for external power input.

Figure 4:
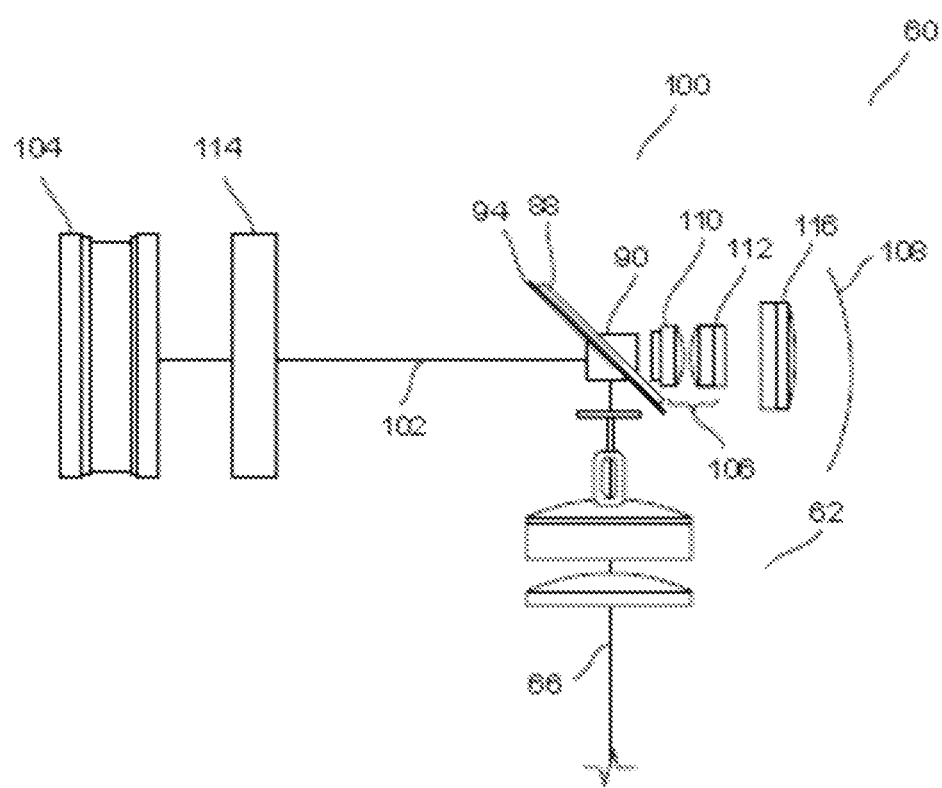
FIG. 4 is a diagrammatic representation of an exemplary embodiment of the retinal imaging device with the illumination module and an imaging module.

FIG. 4 is a diagrammatic representation of the retinal imaging device 60 that includes the illumination module 62 as described in reference to FIG. 3 and an imaging module 100 aligned along an imaging axis 102 and perpendicular to the illumination axis 66. The imaging module 100 includes at least one objective lens 104 to focus the condensed incident beam onto the cornea and a second collimating and projection lens system 106 to focus reflected beam from the retina. In exemplary implementations of the retinal imaging device 60, the light absorber 76 as referred in FIG. 3 may be incorporated in the illumination module 62 or the imaging module 100. In one example, the light absorber 76 is a black dot is on the objective lens 104.

The retinal imaging device as described herein forms a doughnut at the cornea plane as shown in FIG. 2, referred herein as cornea illumination doughnut The outer diameter of the projection lens system 78 and the diameter of the shield 84, determine the dimensions and characteristics of the cornea illumination doughnut. The projected diameter of the outer elliptical stopper 94 at the porosity mirror and the diameter of the protruding hollow cylinder, determine the diameter of the pupil illumination doughnut. Thus the exemplary embodiments as described herein allow for obtaining a reflection free image by the formation of the above referred doughnuts as the two annular imaging rings, one at cornea plane and the other at pupil plane.

The retinal imaging device 60 further includes a viewing module 108 placed in line with the imaging axis 102. In one example the viewing module is a camera lens, in another example the viewing module is a lens for direct viewing by a human eye. In the exemplary implementation a physician may directly view through the viewing module and make observations for an eye being tested. The viewing module can be monocular or binocular. As shown in FIG. 2 the imaging module 100 shares the perforated mirror 88, hollow cylinder 90 and the elliptical shield 94 with the illumination module 62. Further the second collimating and projection lens system 106 may include a series of imaging doublet lenses 110, 112, and 116 as shown in FIG. 2. In one embodiment of the design, an additional image stopper 114 may be provided behind the objective lens 104 for fixing the field of view The lens and other components described herein may be made of a suitable material such as a precisely machined glass. Alternately, transparent plastic materials such as poly (methyl methacrylate), may be used for the purpose provided the refractive index and other optical properties match the requirements of the retinal imaging device. Methods of making precisely machined glass to provide lens to be used in the retinal imaging device are well-known in the art. Further, the relative positioning of each lens with respect to each other are well-known in the art and may be arrived at without undue experimentation by one skilled in the art.

The retinal imaging device 60 as described may further comprise a housing to cover the components described herein. The housing may provide a protective covering against factors such as, environmental factors like water, sunlight, dust, and the like, and also protection against impact during use, transportation, etc. Accordingly, the housing may be made of a suitable material, that may include for example, metals such as steel, cast iron, pig iron, and the like, alloys such as brass, bronze and so on, plastics such as polypropylene, polyethylene, polyethylene terephthalate, and so on. The exact choice of materials to be used may depend on a variety of factors, and may include weight, size and the like. Such materials can be arrived at without undue experimentation by one skilled in the art. The housing may also be provided for aesthetic purposes. This may include colored materials, and may further include symbols being painted on, or embossed upon. Furthermore, the housing may be provided as a multicomponent fixture that has to be fitted together using known means. Having multicomponent pieces enables the opening of a relevant portion of the housing during specific operations, such as servicing. The housing may further have components to allow the device to be affixed to a certain location, or alternately, the device may be used solely as a portable device.

Other additional useful fixtures may form part of the device of the invention, such as a chin registration fixture, a forehead registration fixture, and the like, and combinations thereof. Such fixtures may be in a removable form so as to allow for removal when not in use making the device of the invention compact for transportation and other purposes. In instances where the fixtures are removable, the device may comprise grooves and/or other additional features built into it to allow for facile fitting and removal of the fixtures. Such and other features and fixtures will become obvious to one skilled in the art, and is contemplated to be within the scope of the invention.

For such uses the retinal imaging device is adapted as a handheld portable device that allows for accurate but easy eye testing equipment that can be easily taken to remote geographies where medical facilities may be scarce. For the implementations with a camera module, digital images may be taken by relatively low skilled personnel and the images be stored and may be sent through an appropriate communication means like email, internet, mobile communication to a remote physician, clinic or a hospital for further reading, analysis and reporting.

The advantages of the retinal imaging device, as described herein includes a relative simpler construction allowing for a handheld operation with no extra mounts, adjustment mechanisms or complex electronics for fundus imaging and thus leads to ease of use in the environments where specialized facilities are scarce or not available at all, while still ensuring reflex-free high quality image.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. An illumination module for a retinal imaging device comprising:
   a light source to provide an incident beam along an illumination axis;
   a condenser lens placed at a spaced apart distance from the light source along the illumination axis for condensing the incident beam and emanating a condensed incident beam;
   at least one projection lens system to focus the condensed incident beam along the illumination axis;
   a shield placed at a spaced apart distance from the at least one projection lens system along the illumination axis to yield a first partially blocked beam from the focused condensed incident beam, wherein the first partially blocked beam forms a cornea illumination doughnut in a plane perpendicular to the illumination axis;
   a perforated mirror placed at an angle with respect to the illumination axis;
   a hollow cylinder placed perpendicular to the illumination axis with at least a portion of the hollow cylinder protruding out from a reflecting face of the perforated mirror, wherein a projection of the hollow cylinder forms an elliptical stopper to yield a second partially blocked beam from the focused condensed incident beam to form a pupil illumination doughnut aligned with the cornea illumination doughnut in the plane perpendicular to the illumination axis; and
   wherein an outer diameter of the projection lens system and the diameter of the shield determine the dimensions and characteristics of the cornea illumination doughnut,
   wherein a projected diameter of the elliptical stopper at the perforated mirror and the diameter of the protruding hollow cylinder determine the diameter of the pupil illumination doughnut, and
   wherein the diameter of the cornea illumination doughnut is less than the diameter of the pupil illumination doughnut to yield an annular illumination.

2. The illumination module of claim 1 further comprising a diffuser placed after the light source for receiving the incident beam.

3. The illumination module of claim 1 further comprising a beam splitter placed at a spaced apart distance from the condenser lens.

4. The illumination module of claim 1 wherein the at least one projection lens system is a doublet lens or a combination of lens elements.

5. The illumination module of claim 1 wherein the condenser lens is one of a plano convex lens, a singlet lens, and a combination of lens elements.

6. The illumination module of claim 1 wherein at least one of the condenser lens and the at least one projection lens system is corrected for at least one of spherical aberrations and chromatic aberrations.

7. The illumination module of claim 1 further comprising a transparent plate placed at a spaced apart distance from the condenser lens along the illumination axis, and wherein the transparent plate comprises a light absorber.

8. The illumination module of claim 7 wherein the light absorber is a black dot placed on the transparent plate.

9. The illumination module of claim 1 wherein the light source is one of an LED, a flash tube, a halogen lamp, and a laser light source.

10. A retinal imaging device comprising the illumination module of claim 1.

11. A retinal imaging device comprising:
    an illumination module comprising:
      a light source to provide an incident beam along an illumination axis;
      a condenser lens placed at a spaced apart distance from the light source along the illumination axis for condensing the incident beam and emanating a condensed incident beam;
      at least one projection lens system to focus the condensed incident beam along the illumination axis;
      a shield placed at a spaced apart distance from the at least one projection lens system along the illumination axis to yield a first partially blocked beam from the focused condensed incident beam, wherein the first partially blocked beam forms a cornea illumination doughnut in a plane perpendicular to the illumination axis;
      a perforated mirror placed at an angle with respect to the illumination axis;
      a hollow cylinder placed perpendicular to the illumination axis and at least a portion of the hollow cylinder protruding out from a reflecting face of the perforated mirror, wherein a projection of the hollow cylinder forms an elliptical stopper to yield a second partially blocked beam from the focused condensed incident beam to form a pupil illumination doughnut aligned with the cornea illumination doughnut in the plane perpendicular to the illumination axis; and
    an imaging module aligned along an imaging axis and perpendicular to the illumination axis, the imaging module comprising:
      at least one objective lens to focus the condensed incident beam onto the pupil and the cornea of an eye; and
      a second collimating and projection lens system to focus reflected beams from the retina of the eye; and
    wherein at least one of the illumination module and the imaging module comprises a light absorber.

12. The retinal imaging device of claim 11 wherein the illumination module further comprises a diffuser for receiving the incident beam.

13. The retinal imaging device of claim 11 wherein the illumination module further comprises a beam splitter placed at a spaced apart distance from the condenser lens along the illumination axis.

14. The retinal imaging device of claim 11 wherein the at least one projection lens system is a doublet lens or a combination of lens elements.

15. The retinal imaging device of claim 11 wherein the condenser lens is a plano convex lens or a combination of lens elements.

16. The retinal imaging device of claim 11 wherein the condenser lens is a singlet lens or a combination of lenses.

17. The retinal imaging device of claim 11 wherein at least one of the condenser lens, the at least one projection lens system, the at least one objective lens, and the second collimating and projection lens system is corrected for at least one of spherical aberrations and chromatic aberrations.

18. The retinal imaging device of claim 11 for use in mydriatic or non-mydriatic imaging of the retina.

19. The retinal imaging device of claim 11 further comprising a chin registration fixture, a forehead registration fixture, or combinations thereof.

20. The retinal imaging device of claim 11 wherein the illumination module further comprises a transparent plate with the light absorber placed at a spaced apart distance from the condenser lens along the illumination axis.

21. The retinal imaging device of claim 20 wherein the light absorber is a black dot.

22. The retinal imaging device of claim 21, wherein the black dot is on the at least one objective lens.

23. The retinal imaging device of claim 11 further comprising a monocular or a binocular viewing module placed in line with the imaging axis.

24. The retinal imaging device of claim 23 wherein the viewing module is a lens or a combination of lenses.

25. The retinal imaging device of claim 23 wherein the viewing module is a camera.

26. An illumination module for a retinal imaging device, the illumination module comprising:
- a light source to provide an incident beam along an illumination axis;
- a shield placed at a spaced apart distance from the light source along the illumination axis to yield a cornea illumination doughnut in a plane perpendicular to the illumination axis;
- a perforated mirror placed at an angle with respect to the illumination axis;
- a hollow cylinder with at least a portion of the hollow cylinder positioned through a perforation in the perforated mirror and protruding out from a reflecting face of the perforated mirror; and
- an elliptical stopper formed from a projection of the hollow cylinder to yield a pupil illumination doughnut aligned with the cornea illumination doughnut at an angle to the illumination axis, to yield an annular illumination.

* * * * *